US012096859B2

(12) United States Patent
Kappenman

(10) Patent No.: US 12,096,859 B2
(45) Date of Patent: Sep. 24, 2024

(54) SYSTEM AND METHOD FOR CUSTOMIZING A MATTRESS

(71) Applicant: Kevin J. Kappenman, Huntington Beach, CA (US)

(72) Inventor: Kevin J. Kappenman, Huntington Beach, CA (US)

(73) Assignee: Bed Patent Holdings Limited Liability Company, Las Vegas, NV (US)

( * ) Notice: Subject to any disclaimer, the term of this patent is extended or adjusted under 35 U.S.C. 154(b) by 447 days.

(21) Appl. No.: 17/403,228

(22) Filed: Aug. 16, 2021

(65) Prior Publication Data
US 2022/0053946 A1 Feb. 24, 2022

Related U.S. Application Data

(60) Provisional application No. 63/066,991, filed on Aug. 18, 2020.

(51) Int. Cl.
*A47C 31/12* (2006.01)
*A47C 27/14* (2006.01)
(Continued)

(52) U.S. Cl.
CPC .......... *A47C 31/123* (2013.01); *A47C 27/144* (2013.01); *A61B 5/1036* (2013.01); *A61B 5/107* (2013.01); *G06T 17/00* (2013.01)

(58) Field of Classification Search
CPC ... A47C 31/123; A47C 27/144; A61B 5/1036; A61B 5/107; G06T 17/00
See application file for complete search history.

(56) References Cited

U.S. PATENT DOCUMENTS 8,458,042 B1 6/2013 Roberts et al.
9,456,703 B2 10/2016 O'Mahoney et al.
(Continued)

FOREIGN PATENT DOCUMENTS

| EP | 3023034 | | 5/2016 | |
|----|---------|---|--------|---|
| JP | 2007151817 A | * | 6/2007 | ........... A47C 31/123 |
| KR | 20160137523 A | * | 11/2016 | ........... A47C 31/123 |

OTHER PUBLICATIONS

Scioliosis3DC, "Terms and Definitions", Jul. 12, 2019, https://web.archive.org/web/20190712085214/https://scoliosis3dc.com/scoliosis-resources/terms-and-definitions/ (Year: 2019).*

*Primary Examiner* — Catherine T. Rastovski
*Assistant Examiner* — Yossef Korang-Beheshti
(74) *Attorney, Agent, or Firm* — Blue Capital Law Firm, P.C.

(57) ABSTRACT

A method for customizing a mattress includes acquiring a three dimensional image of a body of a user and preparing, by a processor, a three dimensional model of the body of the user using the three-dimensional image. The method also includes dividing, by the processor, the three dimensional model into a plurality of sections arranged parallel to each other and arrayed along a height of the three dimensional model, and determining a downward pressure to be exerted by each of the plurality of sections on the mattress. The method further includes determining, by the processor, one or more parameters associated with at least one portion of the mattress adapted to be arranged underneath an associated section when person lies on the mattress based on the determined downward pressure or topography.

17 Claims, 8 Drawing Sheets

(51) Int. Cl.
*A61B 5/103* (2006.01)
*A61B 5/107* (2006.01)
*G06T 17/00* (2006.01)

(56) References Cited

U.S. PATENT DOCUMENTS

| | | | | |
|---|---|---|---|---|
| 2011/0056503 | A1* | 3/2011 | Abraham | A61F 5/56 |
| | | | | 128/845 |
| 2015/0029189 | A1* | 1/2015 | O'Mahoney | A47C 31/123 |
| | | | | 345/420 |
| 2018/0148312 | A1* | 5/2018 | Kojima | B68G 7/02 |

\* cited by examiner

| | 4.0 | 8.0 | 12.0 | 16.0 | 20.0 | 24.0 | 28.0 | 32.0 | 36.0 | 40.0 | 44.0 | 48.0 | 52.0 | 56.0 | 60.0 | 64.0 | 68.0 | 69.0 | Total |
|---|---|---|---|---|---|---|---|---|---|---|---|---|---|---|---|---|---|---|---|
| volume | 159.34 | 48.67 | 65.27 | 127.03 | 138.29 | 158.27 | 229.43 | 285.35 | 383.94 | 363.13 | 351.93 | 423.89 | 565.35 | 495.08 | 155.03 | 131.71 | 148.78 | 8.11 | 4238.59 |
| weight | 5.81 | 1.78 | 2.38 | 4.64 | 5.05 | 5.78 | 8.37 | 10.41 | 14.01 | 13.25 | 12.84 | 15.47 | 20.63 | 18.06 | 5.66 | 4.81 | 5.43 | 0.30 | 154.66 |
| PSI - Back | 0.15 | 0.09 | 0.10 | 0.13 | 0.14 | 0.15 | 0.17 | 0.26 | 0.17 | 0.20 | 0.21 | 0.24 | 0.12 | 0.12 | 0.08 | 0.10 | 0.10 | 0.05 | |
| PSI - Side | 0.44 | 0.27 | 0.30 | 0.39 | 0.42 | 0.44 | 0.52 | 0.79 | 0.50 | 0.61 | 0.64 | 0.73 | 0.36 | 0.37 | 0.23 | 0.30 | 0.31 | 0.15 | |
| Lumbar distance | -0.84 | -2.99 | -2.33 | -1.71 | -0.35 | 0.01 | 0.58 | 2.14 | 2.24 | 0.32 | 0.00 | 2.40 | 2.37 | 2.10 | -0.48 | -0.02 | -1.02 | -2.68 | |

SYSTEM AND METHOD FOR CUSTOMIZING A MATTRESS

CROSS-REFERENCE TO RELATED APPLICATIONS

The present Application claims the benefit of U.S. Provisional Patent Application Ser. No. 63/066,991 filed on Aug. 18, 2020, the entire disclosure of which is incorporated herein in its entirety by reference.

FIELD

The present invention pertains to a mattress. More particularly, the present invention pertains to a system and method for assisting a customer to customize or select a mattress according to a body profile of a user.

BACKGROUND

Good sleep is one of the basic necessarily for humans and is desired to provide the human body with adequate rest and repair to the body tissues and brain. Selecting the right mattress becomes essential to provide comfortable and restorative sleep. The right mattress should have anatomical support that is suitable according to the body profile of the user such as body weight, weight distribution, height, BMI, and overall body topography. However, typically mattresses are manufactured based on average body profile of humans that often results in improper postures while sleeping. The improper posture of the user also exaggerates due to the uneven weight distribution of the human body on the mattress.

Methods and systems for customizing the mattress for an individual are known in the art. However, the existing methods and systems customize the mattress based on a two dimensional profile of the individual. These systems and methods, therefore, do not consider concave surfaces of the body, or cannot accurately estimates weight distributions or surface pressures of the individual, which is undesirable.

SUMMARY

According to an aspect of the disclosure, a method for customizing a mattress is disclosed. The method includes acquiring a three dimensional image of a body of a user and preparing, by a processor, a three dimensional model of the body of the user using the three-dimensional image. The method also includes dividing, by the processor, the three dimensional model into a plurality of sections arranged parallel to each other and arrayed along a height of the three dimensional model, and determining a downward pressure to be exerted by each of the plurality of sections on the mattress. The method further includes determining, by the processor, one or more parameters associated with at least one portion of the mattress adapted to be arranged underneath an associated section when person lies on the mattress based on the determined downward pressure.

In one embodiment, the method includes determining a weight of each section by multiplying a volume of each section with a predefined value.

In an embodiment, the predefined value is determined based on a body mass index value of the user.

In an embodiment wherein the downward pressure is a first pressure to be exerted by each section of the plurality of sections on the mattress when the user lies on the mattress on his back.

In an embodiment, the first pressure to be exerted by each section is determined based on a surface area of associated rear surface of the section and a weight of the section.

In an embodiment, the downward pressure is a second pressure to be exerted by each section of the plurality of sections on the mattress when the user lies on the mattress in a side lying position.

In an embodiment, the second pressure to be exerted by each section is determined based on a surface area of associated side surface of the section and a weight of section.

In an embodiment, the method further includes determining a position of a lumber apex of the user in a Y-Z plane, locating a farthest point of each of the plurality of sections relative to the lumber apex, and determining a lumber distance along a z-axis between the apex and farthest point of each of the plurality of sections. The method also includes determining the one or more parameters of the mattress based on the determined lumbar distance of each of the plurality of sections.

In an embodiment, the mattress includes a support structure having a foam layer including a first surface and a second surface arranged opposite to the first surface and defining a plurality of slots extending from the first surface to the second surface and arranged in a plurality of rows. The support structure also includes a plurality of hoop assemblies arranged inside the plurality of slots. Each hoop assembly includes a hoop arranged vertically inside the slot and a central axis of the hoop extends substantially horizontally and parallel to the first surface. The hoop is configured to compress under a load. Further, determining the one or more parameters includes determining at least one of a width or a thickness of the hoop of each hoop assembly adapted to be arranged underneath the associated section.

In an embodiment, the mattress includes an alignment structure supported on the support structure and having an alignment layer having a first surface and a second surface arranged opposite to the first surface and defining a plurality of cut-outs extending from the first surface to the second surface and arranged in a plurality of rows in a staggered arrangement, wherein each cutout of one row partially overlaps with a pair of cutouts arranged in adjacent rows. The one or more parameters includes number of cut-outs, one or more dimensions of the cut-outs, a density of the cut-outs disposed beneath each of the plurality of sections.

According to an aspect of the disclosure a system for customizing a mattress is disclosed. The system includes a processor configured to acquire a three dimensional image of the user, and prepare a three dimensional model of the body of the user using the three-dimensional image. The processor is further configured to divide the three dimensional model into a plurality of sections arranged parallel to each other and arrayed along a height of the three dimensional model. Moreover, the processor is configured to determine a downward pressure to be exerted by each of the plurality of sections on the mattress, and determines one or more parameters associated with at least one portion of the mattress adapted to be arranged underneath one or more of the plurality of sections when person lies on the mattress based on the determined downward pressure.

In an embodiment, the system further includes an image capturing device for capturing the three dimensional image of the body of the user and the processor is in communication with the image capturing device and acquires the three dimensional image from the image capturing device.

In an embodiment, the processor determines a weight of each section by multiplying a volume of each section with a predefined value.

In an embodiment, the downward pressure is a first pressure to be exerted by each section of the plurality of sections on the mattress when the user lies on the mattress on his back.

In an embodiment, the processor determines the first pressure to be exerted by each section based on a surface area of associated rear surface of the section and a weight of the section.

In an embodiment, the downward pressure is a second pressure to be exerted by each section of the plurality of sections on the mattress when the user lies on the mattress in a side lying position.

In an embodiment, the processor determines the second pressure to be exerted by each section based on a surface area of associated side surface of the section and a weight of the section.

In an embodiment, the processor is further configured to determine a position of a lumber apex of the user in a Y-Z plane, and is configured to locate a farthest point of each of the plurality of sections relative to the lumber apex. Moreover, the processor is configured to determine a lumbar distance along a z-axis between the apex and the farthest point of each of the plurality of sections, and is configured to determine the one or more parameters of the mattress based on the determined lumbar distance of each of the plurality of sections.

In an embodiment, the mattress includes a support structure having a foam layer including a first surface and a second surface arranged opposite to the first surface and defining a plurality of slots extending from the first surface to the second surface and arranged in a plurality of rows. The support structure also includes a plurality of hoop assemblies arranged inside the plurality of the slots. Each hoop assembly includes a hoop arranged vertically inside the slot and a central axis of the hoop extends substantially horizontally and parallel to the first surface. The hoop is configured to compress under a load. Further, determining the one or more parameters includes determining at least one of a width or a thickness of the hoop of each of the hoop assembly adapted to be arranged underneath the associated section.

In an embodiment, the mattress includes an alignment structure supported on the support structure and having an alignment layer having a first surface and a second surface arranged opposite to the first surface and defining a plurality of cut-outs extending from the first surface to the second surface and arranged in a plurality of rows in a staggered arrangement. Each cutout of one row partially overlaps with a pair of cutouts arranged in adjacent rows. Moreover, the one or more parameters includes number of cut-outs, one or more dimensions of the cut-outs, a density of the cut-outs disposed beneath each of the plurality of sections.

BRIEF DESCRIPTION OF THE DRAWINGS

FIG. 8 illustrates a table containing data for each section prepared during the method for customizing the mattress, in accordance with an embodiment of the disclosure.

DETAILED DESCRIPTION

Figure 1:
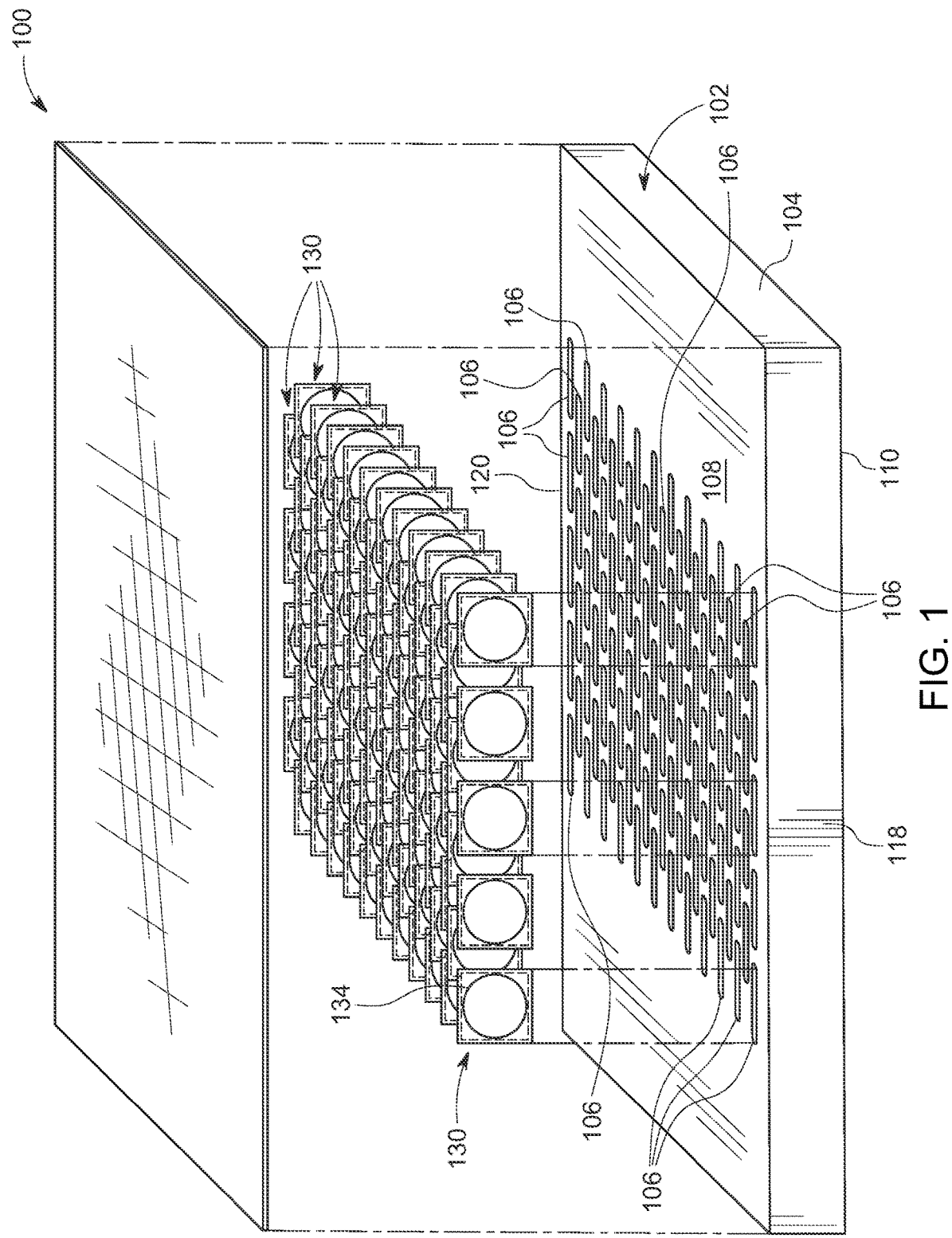
FIG. 1 illustrates a support structure of a mattress, in accordance with an embodiment of the disclosure.
Figure 2:
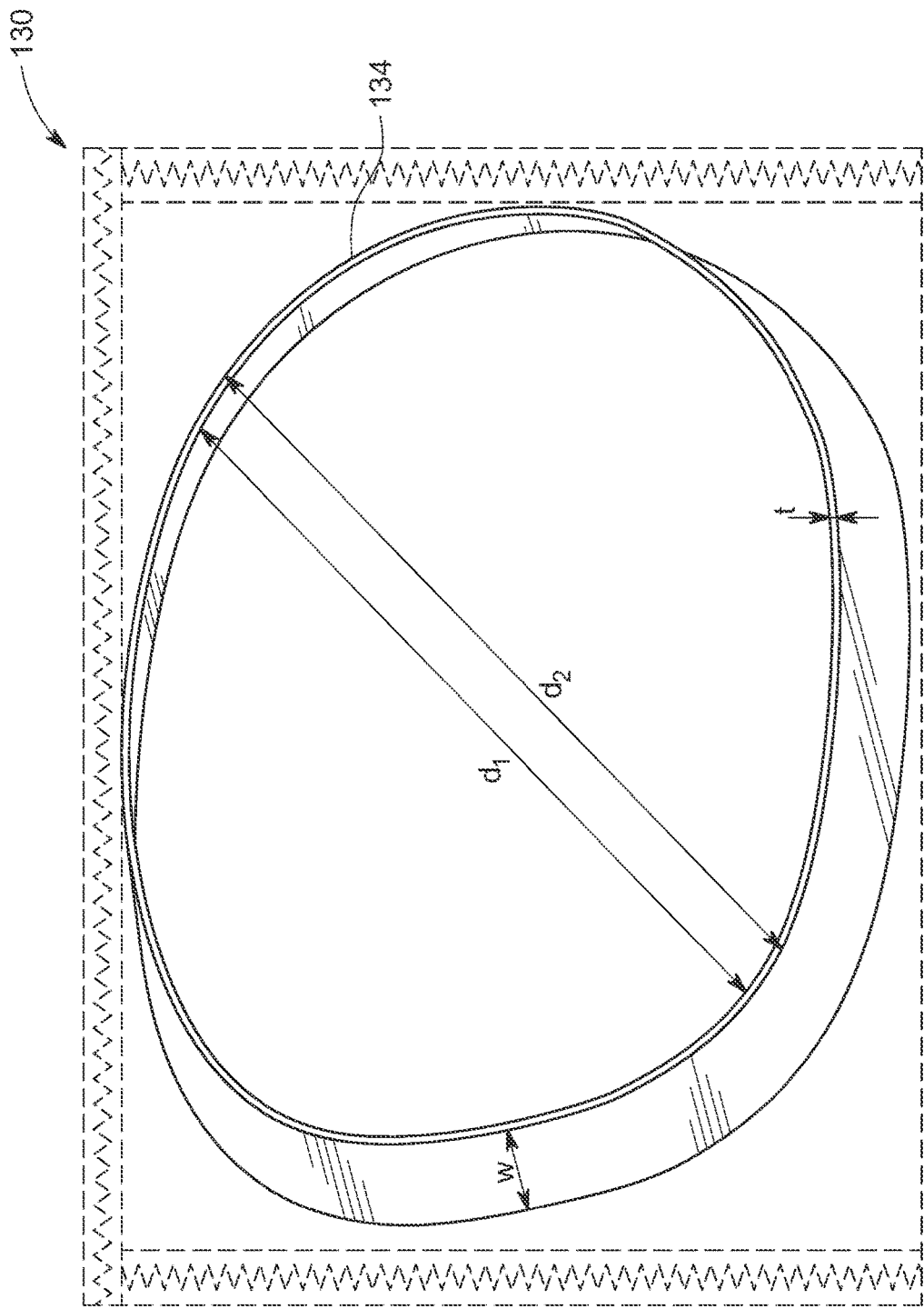
FIG. 2 illustrates a hoop assembly having a hoop of the support structure, in accordance with an embodiment of the disclosure.

Referring to FIG. 1, a support structure 102 for a mattress 100 according to an embodiment is shown, the support structure 102 includes a foam layer 104 defining a plurality of slots 106 extending from a top surface 108 of the foam layer 104 to a bottom surface 110 of the foam layer 104. The plurality of slots 106 is arranged in a plurality of rows extending longitudinally and parallel to a first longitudinal side 118 to a second longitudinal side 120 of the foam layer 104. Further, the slots 106 may be arranged in the plurality of rows in a staggered arrangement or an inline arrangement. Also, the support structure 102 may include a plurality of hoop assemblies 130 disposed inside the plurality of slots 106 such that a single hoop assembly 130 arranged inside a single slot 106. Further, each hoop assembly 130 may include a hoop 134 arranged inside the slot 106 such that a central axis of the hoop 134 is disposed substantially parallel to a horizontal surface (i.e., top surface 108 or bottom surface 110). Therefore, each hoop 134 is arranged inside the slot 106 in a vertical configuration. As shown in FIG. 2, the hoop 134 may be formed by bending a thin rectangular plate into a circular shape. Further, each hoop 134 includes an inner diameter 'd1', an external diameter 'd2', a width 'w', and a thickness 't' that can be varied depending on the required stiffness of support structure 102 (i.e., the mattress 100) or a portion of the support structure 102 (i.e. the mattress 100) corresponding to a portion of the body and weight of the body portion supported by the portion of the support structure 102.

Figure 3:
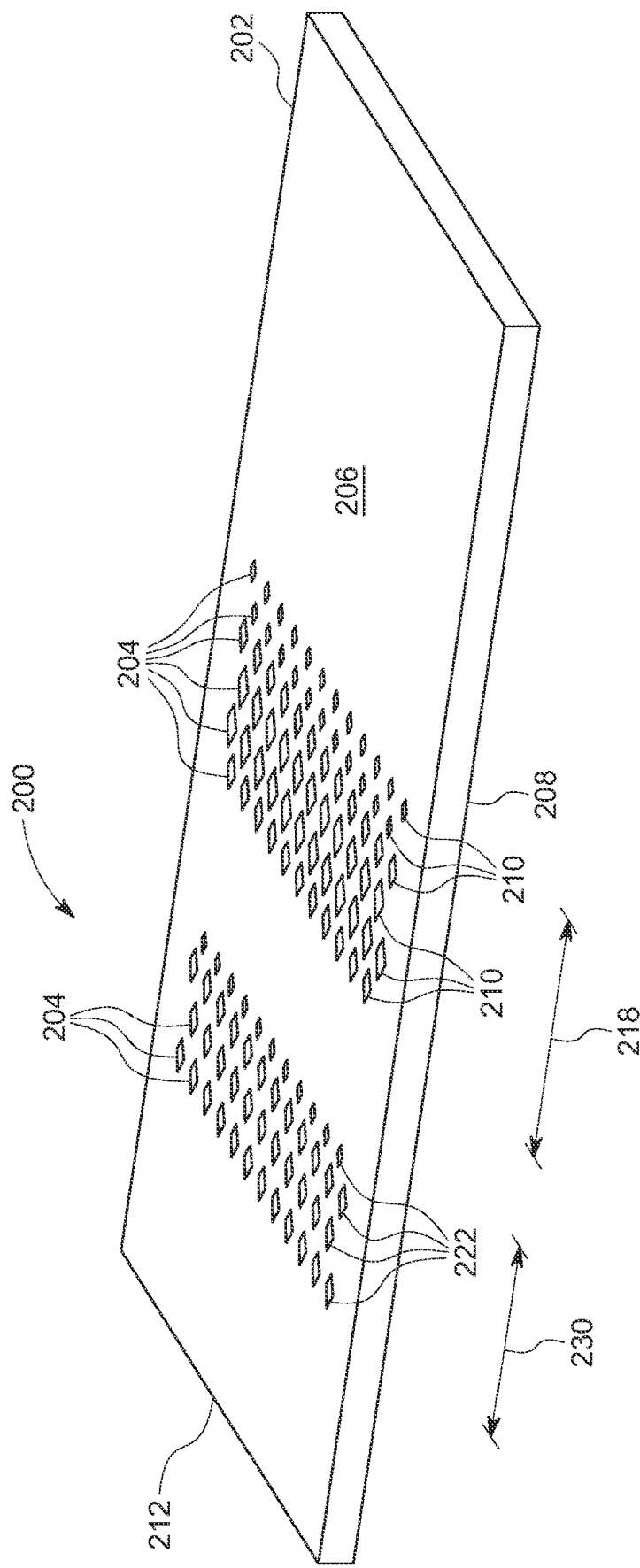
FIG. 3 illustrates an alignment structure of the mattress, in accordance with an embodiment of the disclosure.

Further, the mattress 100 includes an alignment structure 200 (shown in FIG. 3) arranged above the support structure 102 and abutting the support structure 102. The alignment structure 200 facilitates in ergonomically aligning a back portion or a lumber portion of the person/user by providing additional cushioning to a shoulder portion and hip portion when the person/user lies on the mattress 100. The alignment structure 200 may include an alignment layer 202 disposed above the foam layer 104. The alignment layer 202 may be made of a form material and may have a density lesser than a density of the foam layer 104. The alignment layer 202 defines a plurality of cut-outs 204 extending through an entire thickness of the alignment layer 202. As shown, the cut-outs 204 are arranged in a plurality of groups adapted to be disposed beneath and proximate to various body portions of the person/user when the person/user lies on the mattress 100.

In an example, a first group of cut-outs 210 (hereinafter referred to a first cut-outs 210) is disposed beneath and in proximate to a lower back and the hip portion of the person/user when the person lies on the mattress 100. Accordingly, a density of a portion 218 (hereinafter referred to as first portion 218) of the alignment layer 202 having the first cutouts 210 decreases relative to the neighboring areas or portions that are devoid of the first cutouts 210, such as, the areas/portions/regions of the alignment layer 202 adapted to support the lumber region of the person/user. Due to a decrease in the density of the first portion 218, the first portion 218 becomes softer relative to the adjacent areas/regions/portions. Accordingly, a compression of the alignment layer 202 corresponding to the first portion 218 is relatively more than a compression of the alignment layer 202 corresponding to the areas/regions/portions adjacent to the first portion 218 when a person lies on the mattress 100, resulting in proper support to the lumber region of the person. Further, the density of the foam within the first portion 218 may be varied by varying sizes of the first cutouts 210 and spacing between the rows of the first cut-outs 210. In an embodiment, each first cutout 210 may include a diamond shape.

Further, a second group of cut-outs 222 (hereinafter referred to a second cut-outs 222) is adapted to be disposed beneath and in proximate to an upper back and/or the shoulder portion of the person when the person lies on the mattress 100. Further, the second cutouts 222 are disposed between a first longitudinal end 212 of the alignment layer 202 and the first cutouts 204. Due to the presence of second cutouts 222, a density of a portion 230 (hereinafter referred to as second portion 230) having second cutouts 222 decreases relative to the areas/portions/regions disposed adjacent to the portions/regions/areas and are devoid of the second cutouts 222, such as, the area/portion/region of the alignment layer 202 adapted to support the lumber region of the person. Due to the decrease in the density of the second portion 230, the second portion 230 becomes softer relative to the adjacent areas/regions/portions. Accordingly, a compression of alignment layer 202 corresponding to the second portion 230 is relatively more than a compression of the alignment layer 202 corresponding to the portions/regions/areas neighboring the second portion 230 when a person lies on the mattress 100, resulting in proper support to the lumber region of the person. In this manner, the alignment lay may define additional groups of cut-outs to vary the density, softness, and compression of the various portions of the alignment layer.

Further, the density of the foam within the second portion 230 may be varied by varying sizes of the second cutouts 222 and/or varying the spacing between the rows of the second cut-outs 222. In an embodiment, each second cutout 222 may include a diamond shape. Although the cutouts 204 having the diamond shape is contemplated, it may be appreciated that the cutouts 204 may include any other suitable shape, such as, but not limited to, a circular shape, a square shape, an elliptical shape, a rectangular shape, or any other polygonal shape known in the art.

Figure 4:
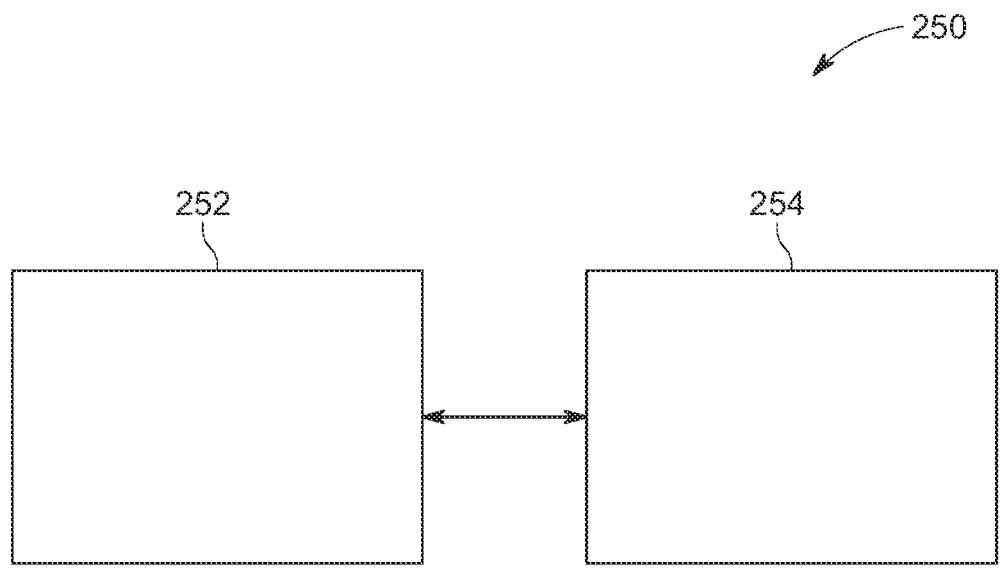
FIG. 4 illustrates a block diagram of a system for customizing the mattress of FIG. 1, in accordance with an embodiment of the disclosure.

A method or process for customizing the mattress 100 according to a body profile and weight distribution of a user is disclosed. The mattress 100 is customized according to the individual user by customizing the support structure 102 and/or the alignment structure 202 based on the body profile and a weight distribution of the body of the individual along a height of the individual. The method is performed by a system 250 shown in FIG. 4 and having an image capturing device 252 adapted to capture a 3-dimensional (3D) image of the body of the user and provide the 3D image to a processor 254 of the system 250 for further processing. In an embodiment, the 3D image is acquired in a 3D point cloud or a mesh format using a suitable image capturing device. In an embodiment, the image capturing device 252 may be a smart phone, a tablet computer or other digital computation peripheral suitable for capturing the 3D image. In an embodiment, the 3D image can be acquired by scanning the body of the user by using LIDAR, photogrammetry, incorporating RGB cameras, infrared projectors and detectors that mapped depth through either structured light or time of flight light calculations. In some embodiments, the processor 254 may receive the 3D image from the user directly. In such a case, the user may create the 3D image using the image capturing device located at his home and shares the 3D image with the system 250 (i.e., the processor 254) via communication system or internet based service. In an embodiment, the processor 254 may synthesize the 3D image of the person by combining and processing multiple 2-dimensional images of the person.

Figure 5:
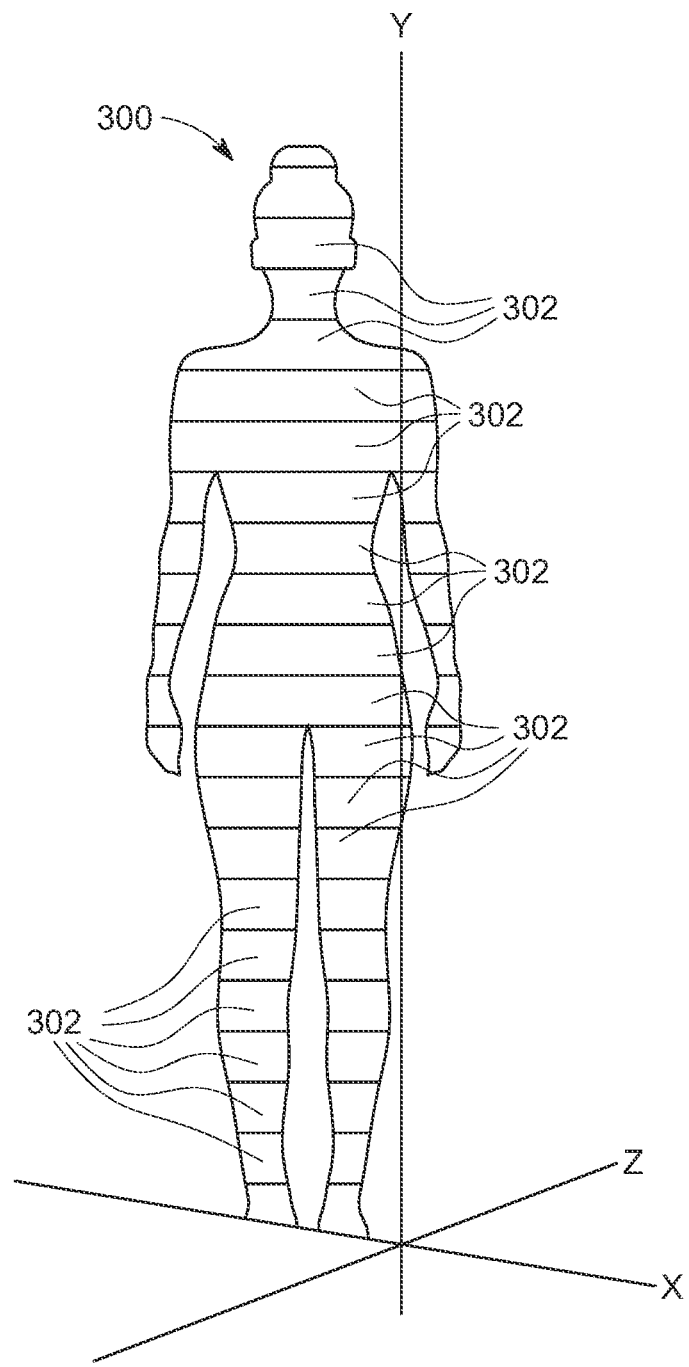
FIG. 5 illustrates a front view of a three dimensional model of the user prepared based on three dimensional image of the user, in accordance with an embodiment of the disclosure.

To determine the body profile and the weight distribution of the body of the individual, the method includes acquiring a three-dimensional (3D) image, by the system 250, of the full body of the user/individual. After acquiring the 3D image of the user, the processor 254 converts the 3D image into a 3D model 300 (shown in FIG. 5). The processor 254 may include various instructions to generate the 3D model 300 from the 3D image. The 3D model 300 includes precise dimensions of the user body facilitating in determining a location and shape of the spine, determining a height, a width of the user's body. Further, the 3D model 300 may be converted into a standard 3D formal file and may be stored in a memory of the system. The 3D model file may be any of the standard format file, such as, but not limited to, an STL, OBJ, FBX, COLLADA, 3DS, IGES; STEP, or VRML/X3D, USZD, etc. In an embodiment, the modeling of the partial body profile can also be done. In the partial body profiling the data may be generated for some particular parts of the body such as but not limited to a hip portion, a lumber curve region, an abdomen region, a torso region from the bottom to the buttocks to facilitate the modeling of the partial profiling of the user.

Subsequent to the preparation of the 3D model 300, the processor 254 may determine/calculate a volumetric weight of the 3D model 300 (hereinafter referred to as model 300), and hence the user's body. The volumetric weight is determined by multiplying a volume of the model 300 with a predefined value. In an embodiment, the predefined value may correspond to a standard volumetric weight value. In an embodiment, the predefined value is 0.584 ounce per cubic inch. In some embodiments, the predefined value is determined by multiplying the standard volumetric weight with by a multiplier depending on body mass index (BMI) value of the user. The multiplier typically varies depending upon the build of a human body. For example, a weight of a muscle of a fat person is low as compared to a weight of a muscle of an athletic person. In this manner the volumetric weight of the model 300, and hence the user's body, is determined.

Thereafter, the processor 254 divides the 3D model into a plurality of sections 302 disposed/arrayed along a height of the model 300 user. The sections 302 may start from a starting point, for example, a lumber apex 'X', and are arrayed in both the direction along the height (i.e., a Y axis). The sections are arranged parallel to each other and dividing planes between the two consecutive sections 302 is parallel to an X-Z plane. After dividing the model 300 into the plurality of sections 302, the processor 254 may determine a weight of each of the sections 302. For so doing, the processor 254 may determine a volume of each of the plurality of sections and multiply the volume of each section by the predefined value.

As such, the processor 254 utilizes the weight of each of the plurality of sections 302 to determine a downward pressure exerted on the mattress 100 when the user lies on the mattress 100. The processor 254 may determine a downward pressure (i.e., a first pressure) exerted by each of the plurality of sections 302 on the mattress 100 when the user lies on the mattress 100 on his/her back. For so doing, the processor 254 may determine a surface area of a rear surface of each of the plurality of sections 302 and divides the weight of each of the plurality of sections 302 by the surface area of a rear surface of the corresponding section 302. In this manner, the first pressure exerted by each of the plurality of sections 302 on the mattress 100 is determined. In some embodiments, the first pressure may be calculated using a surface area corresponding to a front surface of each section 302. It may be appreciated that value of the first pressure exerted by one section 302 may differ from a value of the first pressure exerted by other section 302 depending on the weights of the sections 302 and surface areas of the sections 302.

Also, the processor 254 may determine a downward pressure (i.e., a second pressure) exerted by each of the plurality of sections 302 on the mattress 100 when the user lies on the mattress 100 in a side lying position. For so doing, the processor 254 may determine a surface area of a side surface of each of the sections 302 and divide the weight of the section 302 by the surface area of side surface of the corresponding section 302. In this manner, the pressure exerted by each of the sections 302, when the person is lying in side position, on the mattress 100 is determined. It may be appreciated that value of the second pressure exerted by one section 302 may differ from a value of the second pressure exerted by other section 302 depending on the weights of the sections 302 and surface areas of the sections 302.

Based on the values of the downward pressure, i.e., the first pressure and/or the second pressure, exerted by each section 302 on associated portions of the mattress 100, the processor 254 may determine one or more parameters associated with corresponding portions of the support structure 102 adapted to be disposed beneath the sections 302 of the body of the user. Accordingly, the processor 254 may determine widths 'w' and/or thicknesses 't' of the hoops 130 depending upon the load to be supported and the firmness or stiffness needed for the portion of the mattress 100. In an embodiment, depending on the downward pressure exerted by the sections 302 corresponding to the hip portion and lower back portion, width 'w' and/or a thickness 't' of each hoop 134 adapted to be disposed beneath the hip portion and the lower back portion may be increased relative to hoops 134 adapted to be disposed beneath other portions of the body. Also, the processor 254 may variably determine the inner diameter d1 and the outer diameter d2 of the hoops 134 corresponding to a natural curve of a spine. Therefore, the inner diameter d1 and/or the external diameter d2 of the hoops 134 disposed along a length of the lumber may vary depending on the curvature of the spine of the user. Also, the processor 254 may facilitate in determining densities the foam along various portions of the foam layer 104, densities of the foam of the various portions of the alignment layer 202, and/or a density of the foam of various portions of a top layer 144 (shown in FIG. 1) based on weight of the sections 302 of the model 300, i.e., based on the weight distribution of the body of user. In some embodiment, the one or more parameters may include impression load deflection (ILD) of a layer, for example, the foam layer 104, the alignment layer 202, the top layer 144, or a combination thereof, of the mattress 100. In an embodiment, the processor 254 may facilitate in determining the ILD of various portions of one or more of the foam layers 104, the alignment layer 202, and the top layer 144 based on weight of the sections 302 of the model 300, i.e., based on the weight distribution of the body of user.

The ILD is a measure of the softness or firmness of a foam mattress, or a layer made of foam. ILD is measured by pressing a 12-inch round disk into a 4-inch piece of foam until it presses 25% or one inch into the mattress surface.

Figure 6:
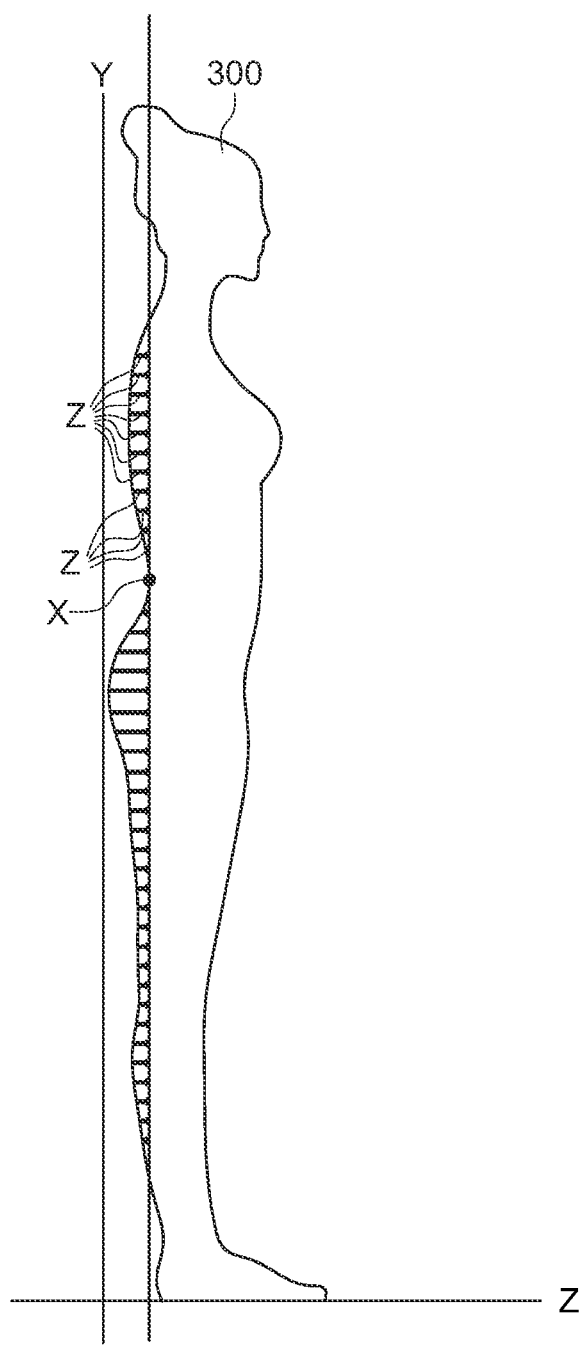
FIG. 6 illustrates a side view of the three dimensional model depicting a lumber apex, in accordance with an embodiment of the disclosure.

Moreover, the processor 254 is adapted to a determine an apex of the lumber curve, i.e., the lumber apex 'X' and determine a position of the lumber apex in a Y-Z plane as shown in FIG. 6. Subsequently, the processor 254 may determine a location of farthest point of a single section 302 relative to the lumber apex 'X' in the y-z plane. Thereafter, the processor 254 may determine a lumber distance 'z' between the lumber apex 'X' and the farthest point of the section 302. The lumber distance 'z' is measure along the z axis. Accordingly, the processor 254 determines a value of the lumber distance 'z' for each of the sections 302. In this manner, the processor is adapted to determine a body profile of the user as viewed in the Y-Z plane. The distance 'z' for each of the sections 302 enables in identifying the lumber curve of the user. Based on the lumber distance 'z' of each of the sections, the processor 254 determines one or more parameters of the alignment structure 200, and therefore facilitates in manufacturing/preparing/designing/customizing the alignment structure 200 according to the body profile of the user.

In an embodiment, the one or more parameters includes number of cut-outs 204, one or more dimensions of the cut-outs 204, a density of the cut-outs 204, etc., disposed beneath each section 302 of the body. The processor 254 selects one or more parameters corresponding to each section 302 based on the distance 'z' associated with the section 302. For example, the size of cutouts 204 is increased or decreased, according to the distance 'z' from the lumbar apex 'X'. In an example, the cutouts 204 adapted to be disposed beneath the section 302 that has a relatively large distance 'z' has greater width relative to the cutouts 204 adapted to be disposed beneath a section that has a relatively smaller distance 'z'. This allows for an ergonomically supportive profile within the mattress. Additionally, the top layer 144 of the mattress 100 can also be modified using the data (body profile and downward pressure). In an example, the processor 254 may determine a density of a foam of the top layer 144 corresponding to an area extending upward from the lumbar apex 'X' to area towards the shoulders to provide a firmer or harder surface according to the customer's preferences.

The method and system for customizing the mattress 100 also facilitates in determining/measuring the support or compressive effects of the individual on an existing bed, thereby assists in a selection of a non-customized mattress that suits the individual body and preference. Further, utilizing the calculated surface pressures in the one or more sections 302 in the hip area, the lumbar area, and the shoulder area, combined with the measured body profile data, a mattress having the customized support structure 102 and/or customized alignment structure 200, and/or customized top layer 144 can be prepared. In addition, the system is capable of capturing the user's profile remotely, for example capturing images on a smart phone or tablet and the mattress may be customized at any another location facilitating in receiving orders from faraway places. Also, the system and the method provide a better and credible recommendation for the mattress 100 to maintain proper posture resulting in reduced muscular or skeleton tension or pressures due to improper posture on the mattress.

Figure 7:
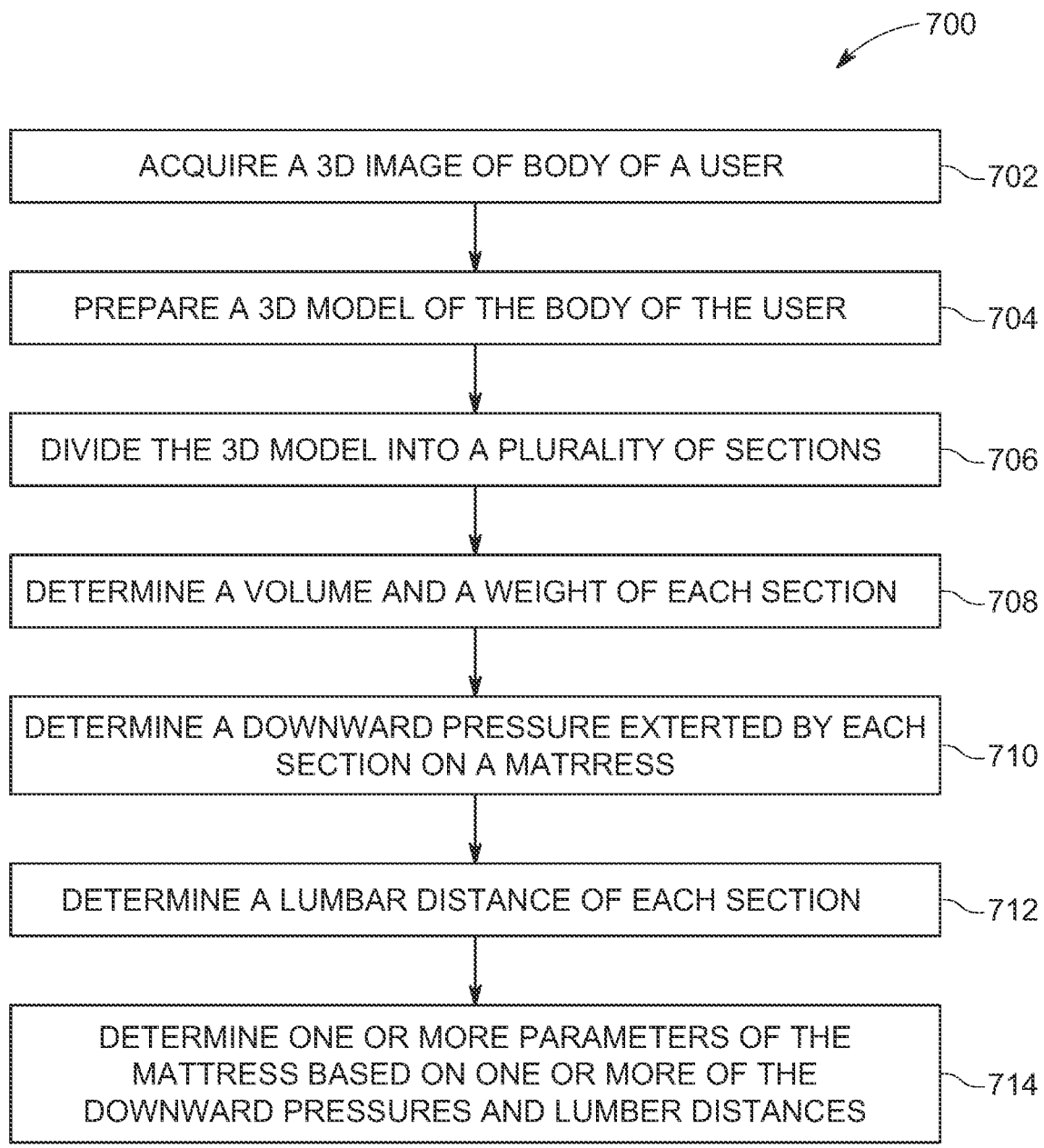
FIG. 7 illustrates a method disclosing various steps involved in customizing the mattress of FIG. 1, in accordance with an embodiment of the disclosure.

An exemplary method 700 (shown in FIG. 7) for preparing the customized mattress 100 is now explained. The method 700 includes a step 702 of capturing/acquiring the 3D image of a body of the user, and a step 704 of converting the 3D image, by the processor 254, into the 3D model 300 of the body of the person. In an embodiment, the processor 254 may receive the 3D image from the image capturing device 252. In an embodiment, the image capturing device may be located at a location remote from the system and in such a case, the processor 254 may acquire the 3D image shared by the user via internet enabled services. Thereafter, at a step 706, the processor 254 divided the 3D model 300 into the plurality of sections 302, each having a predetermined height, for example, a height of 4 inches, arrayed along the height of the 3D model 300, i.e., from a toe to head. The processor 254 stores the data in a tabular manner as shown in FIG. 8, with first row indicating the interval of each section and distance of section from the toe. The first row may be labelled as a header row. As an example, a value of the first column of the first row of the table 800 is indicated as "4.00" and a second section of four inches is defined by "8.00" in a second column of the first row of the table 800. Similarly, the pluralities of sections 302 are defined by their numeric count in the adjacent columns of the first row.

Subsequently, at a step 708, the processor 254 may calculate the volume of each of the sections 302, and may store the volume of each section 302 in the table 800 in a second row of the table 800 labelled as 'volume' as shown in FIG. 8. Thereafter, at the step 708, the processor 254 may determine a weight of each section 302 using volumetric weight of the body. The volumetric weight may be calculated by using BMI as discussed previously. Further, the processor 254 may store the weight of each section 302 in a third row of the table 800, labelled as 'section weight' and tabulates the weight under each section 302 as shown in FIG. 8.

Upon calculating and tabulating the weight of each section 302, the processor 254, at a step 710, may determine a downward pressure, for example, a first pressure "PS1 back" exerted by each of the plurality of sections 302 on the mattress 100 when the user lies on the mattress 100 an his/her back. For so doing, the processor 254 may determine a surface area of a rear surface of each of the plurality of sections 302 and divides the weight of each of the plurality of sections 302 by the surface area of a rear surface of the corresponding section 302. Further, the processor 254 may tabulate data related to the first pressure for each section in a fourth row of the table 800 and label the fourth row as 'PSI-Back'. Similarly, at the step 710, the processor 254 may calculate a downward pressure, i.e., a second pressure 'PSI-Side', of each section 302 by dividing the weight of the section 302 with the corresponding side surface area. Further, the processor 254 may tabulate data related to the second pressure for each section 302 in a fifth row of the table 800 and label the fifth row as 'PSI-Back' as shown in FIG. 8. In addition, the processor 254, at step 712, may determine a lumber distance 'z' value for each section 302 and tabulate the data in a sixth row and label the sixth row as 'lumber distance' as shown in FIG. 8. The processor 254 may determine a value of 'z' for each section as described previously.

Thereafter, at a step 714, the processor 254 determines the one or more parameters of the mattress 100 and customize the mattress 100 according to the value of the one or more of the 'PSI-back, the 'PSI-Side', and the 'lumber distance' for various sections 302. It may be appreciated that the one or more parameters of the support structure 102 and/or one or more parameters of the alignment structure 200 corresponding to each section 302 is determined based on one or more of the 'PSI-back, the 'PSI-Side', and the 'lumber distance. For example, the hoops 134 are customized by increasing support where the PSI-Back is heaviest on the mattress 100. For example, as shown in the table 800, the values of PSI-back is largest corresponding to the sections 32.0, 40.0, 44.0, and 48.0. Therefore, thickness of each hoop 134 adapted to be positioned beneath the sections 32.0, 40.0, 44.0, and 48.0 is made thickener relative to other hoops to create a stronger, more resistive response to compression. Similarly, sizes of the cut-outs beneath the sections 32.0, 40.0, 48.0 may be made larger as compared other cut-outs 204 to increase the compression of the alignment layer 202 adapted to be support the sections 32.0, 40.0, and 48.0. Accordingly, various portions of the mattress 100 are customized according to the body profile and weight distribution of each individual. Additionally, variables identified by the customer such as areas of pain or discomfort, preferred sleeping style (back, side, etc.) and surface comfort preference can be considered when customizing the mattress or individual layers or components of the mattress 100.

Although the method 700 and the system 250 is explained with reference to the mattress 100 having the support structure and/or the alignment structure is explained, it may be envisioned that the steps of the method 700 and the system 250 may be similarly used to facilitate the customization of other mattress, for example, traditionally mattress having the coil springs, to determining one or more parameters of such mattresses. In such a case, the method 700 and system 250 facilitate in determining one or more parameters of one or more coil springs or the foam in which the coil springs are embedded in the foam. For example, the method 700 and the system 250 may enable in identifying a thickness of each of the coil of the coil spring and/or number of coil spring arranged in any area or portion of the mattress. Accordingly, the thicknesses of the coil spring arranged in one area of the mattress may be different from the thicknesses of the coils of the coil springs arranged in another area of the mattress have desired stiffness of the mattress adapted to be arranged under different sections of the body of the user. Similarly, the method 700 or the system 250 may enable in determining and select other parameters of the mattress, for example, size, shape, height, number and strength (gauge) of coil springs. Also, the method and system may enable in determining one or more of Thickness, density, flexibility, pliability, of foam for other support layer, mid mattress layer, or the top layer.

It is also envisioned that the system 250 or the method for customizing the mattress 100 may also determine an amount of compression of the support structure 102 and/or the alignment structure 200 caused by the user when lying on the mattress 100 whether the users are lying on their back, side, stomach, or other sleeping position and may customize the one or more parameters of the mattress 100 accordingly. Users may indicate a preference in the selection process whether they prefer to sleep more on top of the sleep surface or prefer to sink down further into the sleep surface and customize the mattress 100 accordingly. The processor 254 may additionally take into account one or more of areas of discomfort of the user, the sex, and the age of the user while customizing or facilitating in selection of the mattress 100.

It should be understood that the foregoing description is only illustrative of the aspects of the disclosed embodiments. Various alternatives and modifications can be devised by those skilled in the art without departing from the aspects of the disclosed embodiments. Accordingly, the aspects of the disclosed embodiments are intended to embrace all such alternatives, modifications, and variances that fall within the scope of the appended claims. Further, the mere fact that different features are recited in mutually different dependent or independent claims does not indicate that a combination of these features cannot be advantageously used, such as a combination remaining within the scope of the aspects of the disclosed embodiments.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

What is claimed is:

1. A method for customizing or selecting a mattress, the method comprising:
    acquiring, by an image capturing device, a three dimensional image of a body of a user;
    preparing, by a processor, a three dimensional model of the body of the user using the three-dimensional image;
    dividing, by the processor, the three dimensional model into a plurality of sections arranged parallel to each other and arrayed along a height of the three dimensional model;
    determining, by the processor, a downward pressure to be exerted by each of the plurality of sections on the mattress;
    determining, by the processor, a position of a lumbar apex of the user in a Y-Z plane;
    locating, by the processor, a farthest point of each of the plurality of sections relative to the lumbar apex;
    determining, by the processor, a lumbar distance along a z-axis between the lumbar apex and farthest point of each of the plurality of sections;
    determining, by the processor, one or more parameters associated with at least one portion of the mattress adapted to be arranged underneath an associated section of the plurality of sections when the user lies on the mattress based on the determined downward pressure and the determined lumbar distance of each of the plurality of sections; and
    customizing or selecting the mattress based on the determined one or more parameters.

2. The method of claim 1 further including determining a weight of each section by multiplying a volume of each section with a predefined value.

3. The method of claim 2, wherein the predefined value is determined based on a body mass index value of the user.

4. The method of claim 1, wherein the downward pressure is a first pressure to be exerted by each section of the plurality of sections on the mattress when the user lies on the mattress on his back.

5. The method of claim 4, wherein the first pressure to be exerted by each section is determined based on a surface area of associated rear surface of the section and a weight of the section.

6. The method of claim 1, wherein the downward pressure is a second pressure to be exerted by each section of the plurality of sections on the mattress when the user lies on the mattress in a side lying position.

7. The method of claim 6, wherein the second pressure to be exerted by each section is determined based on a surface area of associated side surface of the section and a weight of section.

8. The method of claim 1, wherein the mattress includes a support structure having
    a foam layer including a first surface and a second surface arranged opposite to the first surface and defining a plurality of slots extending from the first surface to the second surface and arranged in a plurality of rows, and
    a plurality of hoop assemblies arranged inside the plurality of the slots, each hoop assembly includes a hoop arranged vertically inside the slot and a central axis of the hoop extends substantially horizontally and parallel to the first surface, wherein the hoop is configured to compress under a load,
    wherein determining the one or more parameters includes determining at least one of a width or a thickness of the hoop of each hoop assembly adapted to be arranged underneath the associated section.

9. The method of claim 8, wherein
    the mattress includes an alignment structure supported on the support structure and having an alignment layer, wherein the alignment layer includes a first surface and a second surface arranged opposite to the first surface and defines a plurality of cut-outs extending from the first surface of the alignment layer to the second surface of the alignment layer and arranged in a plurality of rows in a staggered arrangement, wherein each cutout of one row partially overlaps with a pair of cutouts arranged in adjacent rows, and
    the one or more parameters includes number of cut-outs, one or more dimensions of the cut-outs, a density of the cut-outs disposed beneath each of the plurality of sections.

10. A system for customizing or selecting a mattress, the system comprising:
    an image capturing device to capturing a three dimensional image of a body of a user; and
    a processor arranged in communication with the image capturing device and configured to acquire a three dimensional image of the user from the image capturing device;
    prepare a three dimensional model of the body of the user using the three-dimensional image;
    divide the three dimensional model into a plurality of sections arranged parallel to each other and arrayed along a height of the three dimensional model;
    determine a downward pressure to be exerted by each of the plurality of sections on the mattress;
    determine a position of a lumbar apex of the user in a Y-Z plane;
    locate a farthest point of each of the plurality of sections relative to the lumbar apex;

determine a lumbar distance along a z-axis between the lumbar apex and farthest point of each of the plurality of sections; and determine one or more parameters associated with at least one portion of the mattress adapted to be arranged underneath one or more of the plurality of sections when the user lies on the mattress based on the determined downward pressure and the determined lumbar distance of each of the plurality of sections; and customize or select the mattress based on the determined one or more parameters.

11. The system of claim 10, wherein the processor determines a weight of each section by multiplying a volume of each section with a predefined value.

12. The system of claim 10, wherein the downward pressure is a first pressure to be exerted by each section of the plurality of sections on the mattress when the user lies on the mattress on his back.

13. The system of claim 12, wherein the processor determines the first pressure to be exerted by each section based on a surface area of associated rear surface of the section and a weight of the section.

14. The system of claim 10, wherein the downward pressure is a second pressure to be exerted by each section of the plurality of sections on the mattress when the user lies on the mattress in a side lying position.

15. The system of claim 14, wherein the processor determines the second pressure to be exerted by each section based on a surface area of associated side surface of the section and a weight of the section.

16. The system of claim 10, wherein the mattress includes a support structure having a foam layer including a first surface and a second surface arranged opposite to the first surface and defining a plurality of slots extending from the first surface to the second surface and arranged in a plurality of rows, and a plurality of hoop assemblies arranged inside the plurality of the slots, each hoop assembly includes a hoop arranged vertically inside the slot and a central axis of the hoop extends substantially horizontally and parallel to the first surface, wherein the hoop is configured to compress under a load, wherein determining the one or more parameters includes determining at least one of a width or a thickness of the hoop of each of the hoop assembly adapted to be arranged underneath the associated section.

17. The system of claim 16, wherein the mattress includes an alignment structure supported on the support structure and having an alignment layer, wherein the alignment layer has a first surface and a second surface arranged opposite to the first surface and defines a plurality of cut-outs extending from the first surface of the alignment layer to the second surface of the alignment layer and arranged in a plurality of rows in a staggered arrangement, wherein each cutout of one row partially overlaps with a pair of cutouts arranged in adjacent rows, and the one or more parameters includes number of cut-outs, one or more dimensions of the cut-outs, a density of the cut-outs disposed beneath each of the plurality of sections.

* * * * *